US011008271B2

(12) United States Patent
Yang et al.

(10) Patent No.: US 11,008,271 B2
(45) Date of Patent: May 18, 2021

(54) METHODS FOR THE CONTINUOUS ALKOXYLATION AND DERIVATIZATION OF TERPENES

(71) Applicant: P2 SCIENCE, INC., Woodbridge, CT (US)

(72) Inventors: Yonghua Yang, New Haven, CT (US); Tania Salam, New Haven, CT (US); Patrick Foley, New Haven, CT (US)

(73) Assignee: P2 Science, Inc., Woodbridge, CT (US)

( * ) Notice: Subject to any disclaimer, the term of this patent is extended or adjusted under 35 U.S.C. 154(b) by 0 days.

(21) Appl. No.: 16/331,889

(22) PCT Filed: Sep. 8, 2017

(86) PCT No.: PCT/US2017/050808
§ 371 (c)(1),
(2) Date: Mar. 8, 2019

(87) PCT Pub. No.: WO2018/049252
PCT Pub. Date: Mar. 15, 2018

(65) Prior Publication Data
US 2019/0210948 A1 Jul. 11, 2019

Related U.S. Application Data

(60) Provisional application No. 62/384,939, filed on Sep. 8, 2016.

(51) Int. Cl.
| | |
|---|---|
| C07C 41/06 | (2006.01) |
| C07C 43/162 | (2006.01) |
| C11B 9/00 | (2006.01) |
| A23L 27/20 | (2016.01) |
| B01J 31/10 | (2006.01) |
| C07C 29/04 | (2006.01) |
| C07C 33/025 | (2006.01) |
| C07C 43/178 | (2006.01) |

(52) U.S. Cl.
CPC ............ *C07C 41/06* (2013.01); *A23L 27/203* (2016.08); *B01J 31/10* (2013.01); *C07C 29/04* (2013.01); *C07C 33/025* (2013.01); *C07C 43/162* (2013.01); *C07C 43/1781* (2013.01); *C11B 9/0034* (2013.01); *C11B 9/0053* (2013.01); *A23V 2002/00* (2013.01); *C07C 2601/14* (2017.05); *C07C 2602/28* (2017.05); *C07C 2603/62* (2017.05)

(58) Field of Classification Search
CPC ....... C07C 41/06; C07C 29/04; C07C 33/025; C07C 43/162; C07C 43/1781; C07C 2602/28; C07C 2601/14; C07C 2603/62; A23L 27/203; B01J 31/10; C11B 9/0034; C11B 9/0053; A23V 2002/00
See application file for complete search history.

(56) References Cited

U.S. PATENT DOCUMENTS

| | | | |
|---|---|---|---|
| 3,121,124 A | 2/1964 | Verdol et al. | |
| 4,484,007 A * | 11/1984 | Cardenas | ................ C07C 1/326 568/626 |
| 5,030,768 A | 7/1991 | Chen et al. | |
| 5,531,910 A | 7/1996 | Severns et al. | |
| 6,369,248 B1 * | 4/2002 | Anderson | ............. C07C 69/007 252/8.63 |
| 7,355,066 B1 | 4/2008 | Johnson et al. | |
| 2017/0057940 A1 | 3/2017 | Foley et al. | |
| 2017/0283553 A1 | 10/2017 | Foley et al. | |

FOREIGN PATENT DOCUMENTS

| | | | |
|---|---|---|---|
| CN | 86105408 A | 3/1988 | |
| CN | 102617288 A | 8/2012 | |
| CN | 102964215 A | 3/2013 | |
| CN | 101684064 B | 4/2013 | |
| CN | 103044202 A | 4/2013 | |
| CN | 104926610 B | 9/2016 | |
| WO | WO-9631590 A1 * | 10/1996 | ............... C11D 3/50 |
| WO | WO-2012017447 A2 * | 2/2012 | ............ C07C 29/04 |
| WO | WO 2016/033437 | 3/2016 | |
| WO | WO 2019/028053 | 2/2019 | |

OTHER PUBLICATIONS

P. Lemechko et al., 48 Tetrahedron Letters, 5731-5734 (2007) (Year: 2007).*
R. Parthasarathy et al., 31 Flavour and Fragrance Journal, 120-123 (2016) (Year: 2016).*
CAS Abstract of PRR 450 Catalyst (2012) (Year: 2012).*
CAS Abstract N. Peng et al., Natural Product Letters (2002) (Year: 2002).*
P. Nan et al., Natural Product Letters, 249-253 (2002) (Year: 2002).*
M. Eggersdorfer, in Ullmann's Encyclopedia of Industrial Chemistry, 29-45 (2012) (Year: 2012).*
S. Armando et al, Terpenes: major sources, properties and applications. Monomers, polymers and composites from renewable resources (Elsevier, 2008) (Year: 2008).*
D. Seigler, Plant Secondary Metabolism (1995) (Year: 1995).*
K. Hensen et al., 149 Applied Catalysis A: General, 311-329 (1997) (Year: 1997).*
Y. Liu et al., Industrial & Engineering Chemistry Research, 3170-3175 (2010) (Year: 2010).*
H. Jakobsen, Chemical Reactor Modeling (2008) (Year: 2008).*
CAS Abstract of O-Methylelemol, RN 83426-04-4 (1984) (Year: 1984).*

(Continued)

*Primary Examiner* — Alexander R Pagano
(74) *Attorney, Agent, or Firm* — Hoxie & Associates LLC

(57) ABSTRACT

The invention is directed to methods of producing alkoxylated or hydroxylated terpenes comprising the steps of continuously passing a solution comprising an alcohol in combination with a terpene over an acidic resin catalyst in a packed bed reactor in order to yield a product, as well as compounds that are the products of the methods described herein.

12 Claims, 1 Drawing Sheet

(56) References Cited

OTHER PUBLICATIONS

X. He et al., 122 Chemical Engineering Research and Design, 254-262 (May 6, 2017) (Year: 2017).*

J. Badia et al., Journal of Chemical & Engineering Data, 1054-1064 (2016) (Year: 2016).*

Z. Zhou et al., 114 Chemical Engineering Research and Design, 60-68 (Aug. 10, 2016) (Year: 2016).*

Bai, et al., "Strategies and Methods for the Synthesis of Anticancer Natural Product Neopeltolide and its Analogs," *Curr. Org. Chem.*, vol. 19, No. 10, pp. 871-885, (2015); DOI: 10.2174/1385272819666150119225149.

Da Silva, et al., "Novel Palladium-Catalyzed Oxidative Intramolecular Cyclization of β-Citronellol with H2O2: A Green and Selective Process to Synthesize Oxocine," *Catalysis Letters*, vol. 147, No. 7, pp. 1646-1653, (2017).

Hanson, J., "Chiral Acyclic Synthetic Intermediates from Readily Available Monoterpenoids," *Journal of Chemical Research*, vol. 39, pp. 617-621, (2015).

International Search Report for International Application No. PCT/US2018/044657, dated Sep. 25, 2018, 4 pages.

Pubchem. CID 13469549, Feb. 8, 2007, 11 pages.

Rashid, et al., "Enzymatic Synthesis of Citronellyl Palmitate in Organic Media: Process Optimization and Kinetic Evaluation," Asian Journal of Chemistry, vol. 28, No. 2, pp. 298-300, (2016).

Worzakowska, M., "Thermal Properties of Neryl Long-chain Esters Obtained Under Microwave Irradiation," J. Therm. Anal. Calorim., vol. 120, pp. 1715-1722, (2015); DOI: 10.1007/s10973-015-4489-0.

Written Opinion for International Application No. PCT/US2018/044657, dated Sep. 25, 2018, 7 pages.

Hensen, et al., "Alkoxylation of Limonene and Alpha-pinene Over Beta Zeolite as Heterogeneous Catalyst," *Applied Catalysis A: General*, vol. 149, pp. 311-329, (1997).

Fukumura, et al., "Catalytic Synthesis of Glycerol Monoacetate Using a Continuous Expanded Bed Column Reactor Packed with Cation-Exchange Resin," *Industrial & Engineering Chemistry Research*, vol. 48, No. 4, pp. 1816-1823, (2009); English Abstract Only.

Grudniewska, et al., "Lactones 41. Synthesis and Microbial Hydroxylation of Unsaturated Terpenoid Lactones with p-Menthane Ring Systems," *Molecules*, vol. 18, pp. 2778-2787, (2013); doi: 10.3390/molecules18032778.

International Search Report for International Application No. PCT/US2017/050808, dated Jan. 4, 2018, 4 pages.

Written Opinion for International Application No. PCT/US2017/050808, dated Jan. 4, 2018, 6 pages.

Kleinpeter, et al., "NMR-Untersuchungen an Naturstoffen; Durch Substituenten induzierte Verschiebungen im C-NMR-Spektrum des Elemols," Zeitschrift Fuer Chemie, vol. 22, No. 7, pp. 261-262, (1982); No English Translation.

Radhakrishnan, et al., "Selective Etherification of [beta]-citronellene Catalyzed by Zeolite Beta," Green Chemistry, vol. 17, No. 5, pp. 2840-2845, (2015).

* cited by examiner

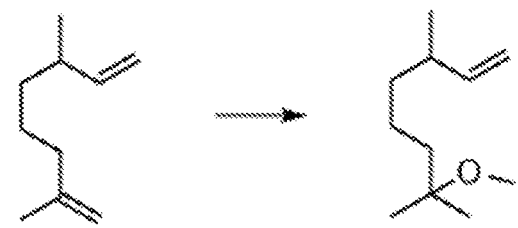 Methoxy-citronellene
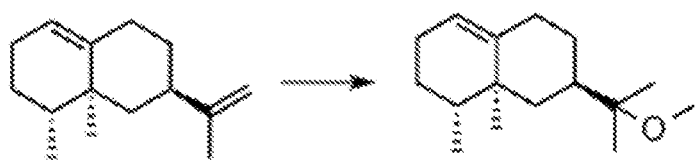 Methoxy-valencene
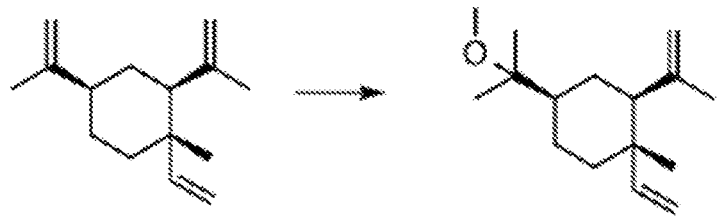 Methoxy-elemene
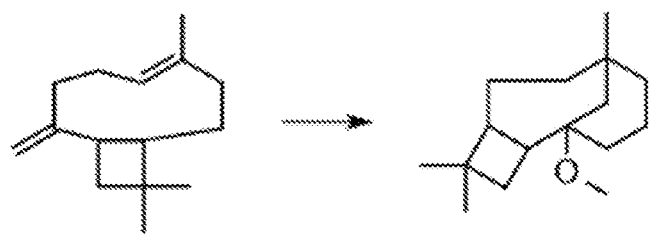 Methoxy-caryophyllene

METHODS FOR THE CONTINUOUS ALKOXYLATION AND DERIVATIZATION OF TERPENES

CROSS-REFERENCE TO RELATED APPLICATIONS

This application is a U.S. National Stage application filed under 35 U.S.C. § 371 of International Application No. PCT/US2017/050808, filed Sep. 8, 2017, which claims the benefit of and priority from U.S. Prov. Appl. No. 62/384,939, filed on Sep. 8, 2016 the entire contents of each of which are incorporated herein by reference.

FIELD OF THE INVENTION

The present invention relates to methods of alkoxylating terpenes. The invention also relates to alkoxylated terpene compounds. The present invention relates generally to a novel process for preparing dihydromyrcenol. More particularly, the present invention relates to methods for making alkoxy-terpenes continuously in a single-step, with high conversion within a short amount of time.

BACKGROUND OF THE INVENTION

Derivatives of terpenes have been widely used in flavors, fragrances, adhesives, pheromones, and cosmetics being made from these renewable starting materials. Existing methods of conversions and derivatizations of terpenes include the thermal conversion of pinane to dihydromyrcene, the conversion of dihydromyrcene to dihydromyrcenol, and the conversion of pinene to limonene. While much work has been focused in this area of research, limited work has been done to improve the continuous reaction of these terpene starting materials using process intensified methods.

Current efforts at producing dihydromyrcenol from dihydromyrcene include: using acidic resins in structured reactors, see, CN 104926610, CN 102964215; using jet reactors, see, Ind. Eng. Chem. Res. 2010, 49, 3170-3175, CN 101684064; and using resin-loaded, reactive distillation columns, see, CN 102617288. These methods all focus solely on hydroxylation chemistry using water under acidic conditions. Because water and the starting material are immiscible, it is required that phase transfer must be overcome through use or additional solvents or through intense mixing. While these methods are of interest for hydroxylation chemistry, there remains a need to develop derivatization chemistry to perform alkoxylations because alkoxy-terpenes are important intermediates and ingredients in the specialty chemicals industry.

For instance, methoxy-citronellene is used both as an ingredient, and as an intermediate for the production of methoxy-melonal, which is a widely used flavor and fragrance agent. Previously, this conversion has only been reported under batch conditions, where the yields are greatly variable and reaction times can range from several hours to days. U.S. Pat. No. 3,121,124 discloses the general etherification of tertiary olefins of this nature using similar chemistry, but fall short of describing the selectivity and reaction demands of terpenes in particular.

In this regard, there is a need for making the alkoxy-terpenes in a much more commercially feasible manner.

BRIEF DESCRIPTION OF THE DRAWINGS

FIG. 1 shows representative alkoxylated terpenes.

BRIEF DESCRIPTION OF THE INVENTION

The invention is related to methods of alkoxylating and hydroxylating terpene compounds. The invention relates to methods which utilize various resins and reaction catalysts in order to alkoxylate and hydroxylate various terpene compounds, continuously in a single-step, with high conversion in a very short amount of time, making this chemistry much more commercially feasible. Additionally, disclosed herein are new molecules that can be used for a wide variety of applications.

The invention further relates to alkoxylated terpene compounds obtained by the methods described herein (e.g., Methods 1.0 et seq). The invention relates to compounds of Formula II and Formula III, described herein.

The invention also relates to uses that pertain to compounds of Formula II, and Formula III.

The invention also relates to methods of hydroxylated compounds obtained by the methods described herein (e.g., Methods 2.0 et seq).

DETAILED DESCRIPTION OF THE INVENTION

In an effort to access a variety of alkoxylated terpenes in a continuous fashion, cationic immobilized resins such as Amberlyst® were explored as a reaction catalyst in packed, structured reactors. In this regard, conversions in very short residence times, e.g., under ten minutes, were at least as high as, or exceeding the conversions observed in comparable batch reaction conditions that can take hours.

While a wide variety of conditions can be used, in a preferred embodiment, ideal conversions could be obtained when methanol was used as a solvent for methoxylation, residence times were below twenty minutes, and the temperature was kept between 50 and 120° C., depending on the substrate. Using this approach, a wide variety of new and existing molecules can be readily prepared, some of which are shown in FIG. 1.

Further a slightly modified approach can be used where a wet alcoholic solution can be used to preferentially form hydroxylated compounds. For example, water in a hindered alcohol such as isopropyl alcohol can be used as the solvent system to make hydroxylates. And any unreacted terpene starting material can be easily recycled through distillation to ensure ultimate conversion to desired product.

The specific approach used here, which can be applied more broadly across different reactor structures and cationic catalyst selection, involved the use of Amberlyst® packed into 6' lengths of ¼" OD (0.21" ID) 316 stainless steel tubing. The tube was then coiled into a roughly 10" diameter coils that were then placed in an oil bath at the desired temperature. Solutions of terpene and alcohol (selected from methanol, isopropanol, ethanol, propanol, butanol, etc.) were then passed through the coils at between 1 and 10 ml/min. Temperatures ranged from 50 to 120° C., with best results often observed at slightly above the boiling point of the given alcoholic solvent. The terpene concentrations were explored between 10% and 50% in the solvent, depending on solubility. In other embodiments, different concentrations could be used.

One very surprising feature of this continuous approach was that a great deal of selectivity was observed. Not only was the tertiary olefin much more readily alkoxylated than the primary olefin found in dihydromyrcene, which one might expect, but a great deal of selectivity was observed between tertiary olefins on the same molecule. For example, when reacting valencene, alkoxylation was strongly preferred on the tertiary olefin pendant (or external to) the ring system. Indeed nearly no alkoxylation was observed on the olefin within the ring system. Further, with regard to elemene, with the two seemingly identical pendant tertiary olefins, there was a very strong selectivity for the slightly less hindered one.

Also surprisingly and of interest was that when caryophyllene was used with methanol, a rearrangement took place, resulting in the methylether depicted in FIG. 1.

With regard to the effects of alcohol, it was observed that the best conversions were observed with methanol, and nearly no alkoxylation was observed with isopropanol. The medium chain alkyl alcohols (ethanol, butanol, propanol) appear to have less conversion to alkoxylates than methanol but more than isopropanol.

The scale-up of this approach can be easily accomplished. For example, a 1" OD 316 stainless steel tube, 6' in length, was also packed with catalyst and operated at the corresponding flow rates and residence times based on volume and catalyst loading. Any number of continuous packed bed configurations can be contemplated for this approach, at nearly any scale provided temperature and residence time are carefully controlled.

Without being bound by any theory, but in one aspect, due to their continuous mode of operation, the reactors (e.g., packed bed reactors) used in the described methods (e.g., Method 1.0, et seq, Method 2.0, et seq) are efficient and exhibit reasonably high throughput rates, but do not allow for the accumulation of intermediates.

Among other things, the terpene-alkoxylates described above can be used as intermediates to derivatize the remaining, "unprotected", olefins. The alkyl-ether can also then be readily converted back to an olefin under appropriate acidic conditions.

The terpene-alkoxylates and hydroxylates can also be used as flavors and fragrances, and cosmetics.

Indeed, in one aspect the invention encompasses Method 1.0, wherein Method 1.0 is a method of producing one or more alkoxylated terpenes, and comprising the steps of: continuously passing a solution comprising an alcohol in combination with a terpene over an acidic resin catalyst in a reactor (e.g., a packed bed reactor) in order to yield a product (e.g., an alkoxylated product).

In certain aspects the invention encompasses the following:

1.1 The method of Method 1.0, wherein said solution is passed at elevated temperature between 50° C. and 120° C.
1.2 The method of Method 1.1, wherein said solution is passed at elevated temperature between 80° C. and 90° C. (e.g., about 80° C.).
1.3 The method of Method 1.0 or 1.1 or 1.2, wherein said acidic resin catalyst is Amberlyst-type cationic exchange resin.
1.4 The method of Method 1.0-1.3, wherein said acidic resin catalyst is a zeolite.
1.5 The method of any of the preceding methods, wherein said product is an alkoxy-adduct of the tertiary olefin of said terpene and said alcohol.
1.6 The method of any of the preceding methods, wherein an average residence time for said solution is between 0 minutes and 30 minutes.
1.7 The method of any of the preceding methods, wherein said alcohol is methanol and said product is methoxylated.
1.8 The method of any of Method 1.0-1.6, wherein said alcohol is ethanol and said product is ethoxylated.
1.9 The method of any of the preceding methods, wherein said terpene is selected from a group comprising monoterpene, sesquiterpene, dihydromyrcene, valencene, elemene, and caryophyllene.
1.10 The method of any of the preceding methods, wherein said terpene is selected from a group consisting of linalool, carene, longifolene, isolongifolene, limonene, menthene, cedrene, dihydromyrcenol, isopulegol, isopulegone, geraniol, citronellol, camphene, thujene, citronellic acid, citronellic acid esters, and pinene.
1.11 The method of any of the preceding methods, wherein said terpene is dihydromyrcene and said alcohol is methanol, thereby forming methoxy-citronellene.
1.12 The method of any of the preceding methods, wherein said terpene is valencene and said alcohol is methanol, and wherein the reaction forms methoxy-valencene.
1.13 The method of any of the preceding methods, wherein the acidic resin catalyst is selected from Silicycle propanesulfonic acid, montmorillonite, or Amberlyst® (e.g., macroreticular or cellular resins or silica covalently bonded to sulfonic acid or carboxylic acid groups).
1.14 The method of any of the preceding methods, wherein the acidic resin catalyst is Amberlyst
1.15 The method of any of the preceding methods, wherein methanol is the alcohol.
1.16 The method of any of the preceding methods, wherein said acidic resin catalyst is packed into a tube or a pipe through which said solution flows.
1.17 The method of any of the preceding methods, wherein products are purified through distillation.
1.18 Any of the preceding methods, wherein the method is utilizes the terpene starting materials described in FIG. 1, and the product are the alkoxylated-terpenes described in FIG. 1.
1.19 Any of the preceding methods, wherein the reactor is a packed bed reactor.

The invention also contemplates any compounds that are obtained or obtainable from any of Method 1.0 et seq. A compound obtained from any of Method 1.0, et seq, can be used as fragrance composition, perfume, soap, candle composition, cosmetic composition, and as a flavoring or flavorant, either as the sole ingredient or as part of a combination of ingredients.

In still a further aspect, the invention also contemplates certain compounds which are the result of any of Method 1.0, et seq. In one aspect the Invention is directed to a Compound 2.0, which is a compound of Formula II described by the following structure:

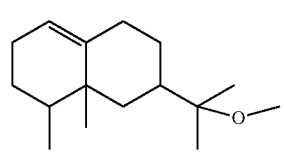

Formula (II)

2.1 The compound of Compound 2.0, wherein the compound is utilized as a synthetic intermediate, or as an ingredient in flavors and fragrances.
2.2 A fragrance composition comprising a compound of Formula (II).
2.3 A perfume composition comprising a compound of Formula (II)
2.4 A soap composition comprising a compound of Formula (II)
2.5 A flavor or flavorant composition comprising a compound of Formula (II).

In one aspect the Invention is directed to a Compound 3.0, which is a compound of Formula III described by the following structure:

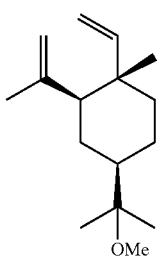

Formula (III)

3.1 The compound of Compound 3.0, wherein the compound is utilized as a synthetic intermediate, or as an ingredient in flavors and fragrances.
3.2 A fragrance composition comprising a compound of Formula (III).
3.3 A perfume composition comprising a compound of Formula (III)
3.4 A soap composition comprising a compound of Formula (III)
3.5 A flavor or flavorant composition comprising a compound of Formula (III).
3.6 The compound of any of the preceding compounds, wherein the starting material used to make the compound of Formula (III) comprises beta-elemene, e.g., described by the following structure:

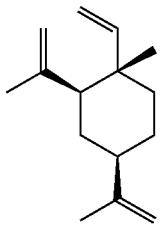

In a further aspect the invention encompasses Method 2.0, which is a method of producing hydroxylated terpenes comprising the steps of: continuously passing a solution comprising an alcohol and water in combination with a terpene over an acidic resin catalyst in a reactor (e.g., a packed bed reactor) in order to yield a product (e.g., a hydroxylated product).

In certain aspects the invention encompasses the following:
2.1 A method of method 2.0, where the terpene is dihydromyrcene and the product is dihydromyrcenol.
2.2 A method of method 2.0 or 2.1, where the alcohol is isopropanol or 2-butanol.
2.3 The method of Method 2.0, 2.1, or 2.2, wherein said solution is passed at elevated temperature between 50° C. and 120° C.
2.4 The method of Method 2.3, wherein said solution is passed at elevated temperature between 80° C. and 90° C. (e.g., about 80° C.).
2.5 The method of any of the preceding methods, wherein said acidic resin catalyst is Amberlyst-type cationic exchange resin.
2.6 The method of any of the preceding methods, wherein said acidic resin catalyst is a zeolite.
2.7 The method of any of the preceding methods, wherein an average residence time for said solution is between 0 minutes and 30 minutes.
2.8 The method of any of the preceding methods, wherein said terpene is selected from a group comprising monoterpene, sesquiterpene, dihydromyrcene, valencene, elemene, and caryophyllene.
2.9 The method of any of the preceding methods, wherein said terpene is selected from a group consisting of linalool, carene, longifolene, isolongifolene, limonene, menthene, cedrene, dihydromyrcenol, isopulegol, isopulegone, geraniol, citronellol, camphene, thujene, citronellic acid, citronellic acid esters, and pinene.
2.10 The method of any of the preceding methods, wherein said terpene is terpene is dihydromyrcene, the alcohol is isopropanol, and the resulting product is dihydromyrcenol.
2.11 The method of any of the preceding methods, wherein the acidic resin catalyst is selected from Silicycle propanesulfonic acid, montmorillonite, or Amberlyst® (e.g., macroreticular or cellular resins or silica covalently bonded to sulfonic acid or carboxylic acid groups).
2.12 The method of any of the preceding methods, wherein the acidic resin catalyst is Amberlyst®.
2.13 The method of any of the preceding methods, wherein said acidic resin catalyst is packed into a tube or a pipe through which said solution flows.
2.14 The method of any of the preceding methods, wherein the products are purified through distillation.
2.15 The method of any of the preceding methods, wherein the alcohol is isopropanol or 2-butanol.

The invention also contemplates any compounds that are obtained or obtainable from any of Method 2.0 et seq. A compound obtained from any of Method 2.0, et seq, can be used as fragrance composition, perfume, soap, candle composition, cosmetic composition, and as a flavoring or flavorant, either as the sole ingredient or as part of a combination of ingredients.

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below. All percentages used herein, unless otherwise indicated, are by volume.

In the present specification, the structural formula of the compounds represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formulas described herein, it is noted that any crystal form, crystal form mixture, or anhydride or hydrate thereof is included in the scope of the present invention.

All ratios used herein, unless otherwise indicated, are by molarity.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" or "encompassing" is not intended to be limiting and is used in the same way that the term "comprising" is commonly used.

In some formulae of the present application, one or more chiral centers are identified by an asterisk placed next to the chiral carbon. In other formulae, no chiral center is identified, but the chiral isomers are nonetheless covered by these formulae.

Some compounds of the present invention can exist in a tautomeric form which is also intended to be encompassed within the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group typically although not necessarily containing 1 to about 12 carbon atoms, such as methyl, ethyl, n-propyl, isopropyl, n-butyl, isobutyl, t-butyl, octyl, and the like.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like.

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

In at least one aspect, the methods described herein (e.g., Method 1.0, et seq., Method 2.0, et seq) utilize packed bed reactors. And, the compounds described herein, e.g., Formula (II), Formula (III), or any compound obtained from any of Method 1.0 et seq or Method 2.0 et seq) can be obtained by utilizing a "Packed bed reactors". These reactors are tubular and in some aspects are filled with solid catalyst particles, and can be used to catalyze gas reactions. At least one advantage of using a packed bed reactor can be the higher conversion per weight of catalyst than other catalytic reactors. The conversion is based on the amount of the solid catalyst rather than the volume of the reactor.

As used herein, the term "fragrance composition" means a mixture of fragrance ingredients, e.g., including the compounds of Formula II, and Formula III, and compounds that are obtained or obtainable from any of Method 1.0, et seq. or Method 2.0, et seq, including auxiliary substances if desired, dissolved in a suitable solvent or mixed with a powdery substrate used to provide a desired odor to a product.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furans, ketals, nitriles, acids, and hydrocarbons, including both saturated and unsaturated compounds and aliphatic carbocyclic and heterocyclic compounds, and animal products.

Fragrance and ingredients and mixtures of fragrance ingredients that may be used in combination with the disclosed compounds (e.g, compounds of Formula II, Formula III, or a compound obtain by any of Method 1, et seq. or a compound obtain by any of Method 2, et seq.) for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

Invention also contemplates the method of using a Compound of Formulas II, or III, and/or a compound obtained by any of Method 1.0 et seq or a compound obtained by any of Method 2.0 et seq, in a composition selected from the following: a fragrance composition, perfume, soap, and as a flavoring or flavorant.

In some embodiments, the product of the method of the invention may contain more than about 80% of compound of Formulas (II), (III), or any compound obtained by Method 1.0 et seq., or any compound obtained by Method 2.0 et seq. In some embodiments, the product of the method of the invention (e.g., compound of formulas, (II), (III), or any compound obtain by Method 1.0 et seq., or any compound obtained by Method 2.0 et seq) may contain more than about 85%, more than about 90%, more than about 92%, more than about 95%, more than about 97%, more than about 98%, more than about 98.5%, or more than about 99%. In accordance with the aspects of the invention discussed herein, the product (e.g., compound of formulas, (II), (III), or any compound obtain by Method 1.0 et seq., or any compound obtained by Method 2.0 et seq) may contain less than about 20%, less than about 15%, less than about 10%, less than about 8%, less than about 3%, less than about 2%, less than about 1.5%, or less an about 1% impurities.

In accordance with these embodiments, the product (e.g., compound of formulas, (II), (III), or any compound obtain by Method 1.0 et seq., or any compound obtained by Method 2.0 et seq) may contain less than about 20%, less than about 15%, less than about 10%, less than about 8%, less than about 3%, less than about 2%, less than about 1.5%, or less an about 1% impurities.

As used herein, "perfume composition" means a mixture of fragrance materials, including auxiliary substances if desired, dissolved in a suitable solvent or mixed with a powdery substrate used to impart a desired odor to a product. In one aspect, "perfume compositions" described herein can comprise any of the compound of formulas, (II), (III), or any compound obtained by Method 1.0 et seq., or any compound obtained by Method 2.0 et seq, can. In a further aspect, any of the compound of formulas, (II), (III), or any compound obtained by Method 1.0 et seq., or any compound obtained by Method 2.0 et seq, can be used as part of any of the foregoing examples of products having perfume compositions which include, but are not limited to, perfumes, soaps, detergents, air fresheners, room sprays, pomanders, candles, cosmetics, such as creams, ointments, toilet waters, pre- and aftershave lotions, talcum powders, hair-care agents, body deodorants and anti-perspirants. Fragrance materials and mixtures of fragrance materials that may be used in combination with the disclosed compounds for the manufacture of a perfume compositions include, but are not limited to, natural products including essential oils, absolutes, resinoids, resins, and concretes, and synthetic fragrance materials which include, but are not limited to, hydrocarbons, alcohols, aldehydes, ketones, ethers, acids, esters, acetals, ketals, and nitriles, including both saturated and unsaturated compounds and aliphatic carbocyclic and heterocyclic compounds.

Examples of the fragrance materials which may be used in combination with the disclosed (e.g., compounds of Formula II, Formula III, and a compound obtained by any of Method 1, et seq., or a compound obtained by any of Method 2, et seq.) include but are not limited to, geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedimethylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks.

Auxiliary substances and solvents which may be used in perfume compositions containing compounds according to the present invention include, but are not limited to, ethanol, isopropanol, dipropylene glycol, dipropyleneglycol monomethyl ether, and diethylphthalate.

The quantities of the disclosed compounds used in a fragrance or perfume or cosmetic composition or a product to be perfumed may vary according to the nature of the product, the nature and quantity of the other fragrance materials in the flavor, fragrance, perfume, soap, or cosmetic composition, and on the desired odor effect. For example, any of the compound of formulas, (II), (III), or any compound obtained by Method 1.0 et seq., or any compound obtained by Method 2.0 et seq may be found in a given flavor, fragrance, perfume, soap, or cosmetic composition from 0.005% to 25%, by weight of the composition, from 0.05% to 10%, by weight of the composition, or more particularly, from 0.1% to 5% by weight of the composition.

EXPERIMENTAL

General Reaction Apparatus

A Syrris syringe pump was used to pump solutions of alcohol and terpene into the resin packed reactors at a preset follow rate. When the alcohol and terpene were immiscible, a magnetic stir plate and stir bar was used to vigorously stir the mixture being pumped. The reactors constructed of 316 stainless steel tubing, were packed with Amberlyst® 15(H) resin, and were heated in an oil bath at the desired temperature. Residence times were calculated using volumes calculated from random close packing (RCP) of spheres assumptions and the volume of the tube.

An Agilent 6890N GC equipped with a Stabilwax® 30 meter (0.25 mm ID) column was used to monitor the reactions. Conversion was calculated based on disappearance of starting material and desired product composition was determined based on peak integration. Retention times of products were based on analytical standards. $^1$H NMR and $^{13}$C NMR were used to confirm the identity of all molecules.

Example 1: Preparation of Methoxy-Citronellene 105 g (0.76 mol) of dihydromyrcene was dissolved in 135 g of methanol (4.22 mol). This clear solution was then pumped at a flow rate of 1.25 ml/min through the packed reactor at a temperature of 80-84° C. The reactor was chased with methanol and the bulk at the end of the reaction run showed the material to be 33.1% starting material (dihydromyrcene) and 53.9% methoxy-citronellene. The material was set aside for purification through distillation.

Example 2: Preparation of Methoxy-Valencene 150 g (0.734 mol) of valencene (81.65% pure) was dissolved in 110 g (3.44 mol) methanol. This mixture was pumped at a flow rate of 2.5 ml/min through the reactor which was heated at 80° C. A sample of the reaction mixture indicated that there was 9.14% valencene starting material and 45.4% methoxy-valencene product. The reactor was chased with methanol and the reaction mixture was concentrated and purified by distillation. Many fractions were collected, including a 53.3 g major fraction of material that was 82.9% pure by GC. Additional pure material was obtained through column chromatography.

NMR data is as follows: (3R,4aS,5R)-3-(2-methoxypropan-2-yl)-4a,5-dimethyl-1,2,3,4,4a,5,6,7-octahydronaphthalene (aka Methoxy-Valencene)

$^1$H NMR (CDCl$_3$, 500 MHz), δ 0.87 (d, 3H, —CH$_3$), 0.93 (s, 3H, —CH$_3$), 0.98-1.02 (m, 1H, —CH—), 1.03-1.12 (m, 2H, —CH$_2$—), 1.06 (s, 3H, —CH$_3$), 1.09 (s, 3H, —CH$_3$), 1.40-1.42 (m, 2H, —CH$_2$—), 1.73-2.10 (m, 6H, —CH$_2$—, —CH—), 2.23-2.30 (m, 1H, —CH—), 3.36 (s, 3H, —OCH$_3$), 5.31 (t, J=2.5 Hz, 1H, —CH=C).

Example 3: Preparation of Ethoxy-Valencene 12 g (0.059 mol) of valencene (81.65% pure) was dissolved in 68 g of ethanol. This mixture was pumped at a flow rate of 2.5 ml/min through the reactor which was heated at 100° C. A sample of the reaction mixture indicated that there was a significant amount of starting material and ~9.25% ethoxy-nootkatone product. Similar conditions were used to prepare Methoxy-Elemene and Methoxy-Caryophyllene.

NMR data for Methoxy-Elemene is as follows: (1R,2S,4R)-4-(2-methoxypropan-2-yl)-1-methyl-1,2-di(prop-1-en-2-yl)cyclohexane (aka Methoxy-Elemene)

$^1$H-NMR (CDCl$_3$, 500 MHz): δ 0.98 (d, 3H, —CH$_3$), 1.12 (s, 6H, —CH$_3$), 1.24-1.31 (m, 1H, —CH—), 1.42-1.45 (m, 3H, —CH$_2$—), 1.49-1.61 (m, 3H, —CH$_2$—, —CH—), 1.71 (s, 3H, —CH$_3$), 1.95 (dd, J=12.5 Hz, J=3.0 Hz, 1H, —CH—), 3.17 (s, 3H, —OCH$_3$), 4.58 (t, J=1.5 Hz, 1H, —CH=), 4.81 (t, J=1.5 Hz, 1H, —CH=), 4.87 (s, 1H, —CH=), 4.90 (dd, J=8.0 Hz, J=1.5 Hz, 1H, CH=), 5.81 (dd, J=17.5 Hz, J=1.0 Hz, 1H, CH=)

Example 4: Preparation of Dihydromyrcenol

A homogenous mixture of dihydromyrcene (20 g), water (20 g), and isopropanol (65 g) is pumped through a heated column (⅜" OD, 0.028" wall thickness, 6 feet long) packed with Amberlyst 15 at a rate of 1.5 mL/min at 100° C. GC showed there was 13.8% dihydromyrcenol formed with 68.6% dihydromyrcene residual that can be recycled back into the column following distillation.

The invention claimed is:

1. A method of producing an alkoxylated terpene comprising the step of: continuously passing a solution comprising methanol, in combination with the terpene over an acidic resin catalyst in a packed bed reactor in order to yield a product, wherein the acidic resin catalyst is selected from a propanesulfonic acid resin, or a montmorillonite, or a macroreticular or cellular resin covalently bonded to sulfonic acid or carboxylic acid groups, or a silica covalently bonded to sulfonic acid or carboxylic acid groups, and wherein said terpene is valencene.

2. The method of claim 1, wherein the average residence time for said solution in the packed bed reactor is between 0 minutes and 30 minutes.

3. The method of claim 1, wherein said acidic resin catalyst is packed into a tube or a pipe through which said solution flows.

4. The method of claim 1, wherein products are purified through distillation.

5. A compound of Formula (II) described by the following structure:

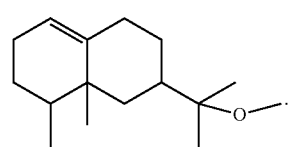

Formula (II)

6. A fragrance composition, perfume composition, soap composition, flavor composition, or flavorant composition, comprising a compound according to claim 5.

7. The method of claim 1, wherein the acidic resin catalyst is a silica covalently bonded to sulfonic acid or carboxylic acid groups.

8. The composition according to claim 6, wherein the composition is a fragrance composition.

9. The composition according to claim 6, wherein the composition is a perfume composition.

10. The composition according to claim 6, wherein the composition is a soap composition.

11. The composition according to claim 6, wherein the composition is a flavor composition.

12. The composition according to claim 6, wherein the composition is a flavorant composition.

* * * * *

UNITED STATES PATENT AND TRADEMARK OFFICE
CERTIFICATE OF CORRECTION

Page 1 of 2

PATENT NO. : 11,008,271 B2
APPLICATION NO. : 16/331889
DATED : May 18, 2021
INVENTOR(S) : Yang et al.

It is certified that error appears in the above-identified patent and that said Letters Patent is hereby corrected as shown below:

On the Title Page

Delete the title page and substitute therefore with the attached title page.

In the Claims

Column 12, Line 52, immediately after Claim 12 and before the asterisks, insert Claims 13 and 14 as follows:
--13. The method of claim 1, wherein said solution is passed at elevated temperature of between 50° C. and 120° C.
14. The method of claim 1, wherein the acidic resin catalyst is a macroreticular or cellular resin covalently bonded to sulfonic acid or carboxylic acid groups.--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

(12) United States Patent
Yang et al.

(10) Patent No.: US 11,008,271 B2
(45) Date of Patent: May 18, 2021

(54) METHODS FOR THE CONTINUOUS ALKOXYLATION AND DERIVATIZATION OF TERPENES

(71) Applicant: P2 SCIENCE, INC., Woodbridge, CT (US)

(72) Inventors: Yonghua Yang, New Haven, CT (US); Tania Salam, New Haven, CT (US); Patrick Foley, New Haven, CT (US)

(73) Assignee: P2 Science, Inc., Woodbridge, CT (US)

(*) Notice: Subject to any disclaimer, the term of this patent is extended or adjusted under 35 U.S.C. 154(b) by 0 days.

(21) Appl. No.: 16/331,889

(22) PCT Filed: Sep. 8, 2017

(86) PCT No.: PCT/US2017/050808
§ 371 (c)(1),
(2) Date: Mar. 8, 2019

(87) PCT Pub. No.: WO2018/049252
PCT Pub. Date: Mar. 15, 2018

(65) Prior Publication Data
US 2019/0210948 A1 Jul. 11, 2019

Related U.S. Application Data
(60) Provisional application No. 62/384,939, filed on Sep. 8, 2016.

(51) Int. Cl.
C07C 41/06 (2006.01)
C07C 43/162 (2006.01)
C11B 9/00 (2006.01)
A23L 27/20 (2016.01)
B01J 31/10 (2006.01)
C07C 29/04 (2006.01)
C07C 33/025 (2006.01)
C07C 43/178 (2006.01)

(52) U.S. Cl.
CPC ............ C07C 41/06 (2013.01); A23L 27/203 (2016.08); B01J 31/10 (2013.01); C07C 29/04 (2013.01); C07C 33/025 (2013.01); C07C 43/162 (2013.01); C07C 43/1781 (2013.01); C11B 9/0034 (2013.01); C11B 9/0053 (2013.01); A23V 2002/00 (2013.01); C07C 2601/14 (2017.05); C07C 2602/28 (2017.05); C07C 2603/62 (2017.05)

(58) Field of Classification Search
CPC ....... C07C 41/06; C07C 29/04; C07C 33/025; C07C 43/162; C07C 43/1781; C07C 2602/28; C07C 2601/14; C07C 2603/62; A23L 27/203; B01J 31/10; C11B 9/0034; C11B 9/0053; A23V 2002/00
See application file for complete search history.

(56) References Cited

U.S. PATENT DOCUMENTS

| | | |
|---|---|---|
| 3,121,124 A | 2/1964 | Verdol et al. |
| 4,484,007 A * | 11/1984 | Cardenas ............ C07C 1/326 568/626 |
| 5,030,768 A | 7/1991 | Chen et al. |
| 5,531,910 A | 7/1996 | Severns et al. |
| 6,369,248 B1 * | 4/2002 | Anderson ............ C07C 69/007 252/8.63 |
| 7,355,066 B1 | 4/2008 | Johnson et al. |
| 2017/0057940 A1 | 3/2017 | Foley et al. |
| 2017/0283553 A1 | 10/2017 | Foley et al. |

FOREIGN PATENT DOCUMENTS

| | | | |
|---|---|---|---|
| CN | 86105408 A | 3/1988 | |
| CN | 102617288 A | 8/2012 | |
| CN | 102964215 A | 3/2013 | |
| CN | 101684064 B | 4/2013 | |
| CN | 103044202 A | 4/2013 | |
| CN | 104926610 B | 9/2016 | |
| WO | WO-9631590 A1 * | 10/1996 | ............ C11D 3/50 |
| WO | WO-2012017447 A2 * | 2/2012 | ............ C07C 29/04 |
| WO | WO 2016/033437 | 3/2016 | |
| WO | WO 2019/028053 | 2/2019 | |

OTHER PUBLICATIONS

P. Lemechko et al., 48 Tetrahedron Letters, 5731-5734 (2007) (Year: 2007).*
R. Parthasarathy et al., 31 Flavour and Fragrance Journal, 120-123 (2016) (Year: 2016).*
CAS Abstract of PRR 450 Catalyst (2012) (Year: 2012).*
CAS Abstract N. Peng et al., Natural Product Letters (2002) (Year: 2002).*
P. Nan et al., Natural Product Letters, 249-253 (2002) (Year: 2002).*
M. Eggersdorfer, in Ullmann's Encyclopedia of Industrial Chemistry, 29-45 (2012) (Year: 2012).*
S. Armando et al, Terpenes: major sources, properties and applications. Monomers, polymers and composites from renewable resources (Elsevier, 2008) (Year: 2008).*
D. Seigler, Plant Secondary Metabolism (1995) (Year: 1995).*
K. Hensen et al., 149 Applied Catalysis A: General, 311-329 (1997) (Year: 1997).*
Y. Liu et al., Industrial & Engineering Chemistry Research, 3170-3175 (2010) (Year: 2010).*
H. Jakobsen, Chemical Reactor Modeling (2008) (Year: 2008).*
CAS Abstract of O-Methylelemol, RN 83426-04-4 (1984) (Year: 1984).*

(Continued)

*Primary Examiner* — Alexander R Pagano
(74) *Attorney, Agent, or Firm* — Hoxie & Associates LLC

(57) ABSTRACT

The invention is directed to methods of producing alkoxylated or hydroxylated terpenes comprising the steps of continuously passing a solution comprising an alcohol in combination with a terpene over an acidic resin catalyst in a packed bed reactor in order to yield a product, as well as compounds that are the products of the methods described herein.

14 Claims, 1 Drawing Sheets